(12) United States Patent
Matahira et al.

(10) Patent No.: US 6,855,727 B2
(45) Date of Patent: Feb. 15, 2005

(54) MUSCULAR FATIGUE-CONTROLLING COMPOSITION AND METHOD FOR PROVIDING MUSCULAR FATIGUE-CONTROLLING EFFECT

(75) Inventors: Yoshiharu Matahira, Shimada (JP); Kazuaki Kikuchi, Hujieda (JP)

(73) Assignee: Yaizu Suisankagaku Industry Co., Ltd., Yaizu (JP)

( * ) Notice: Subject to any disclaimer, the term of this patent is extended or adjusted under 35 U.S.C. 154(b) by 0 days.

(21) Appl. No.: 09/933,438

(22) Filed: Aug. 20, 2001

(65) Prior Publication Data

US 2002/0103244 A1 Aug. 1, 2002

(30) Foreign Application Priority Data

Dec. 4, 2000 (JP) ........................................ 2000-368299
May 15, 2001 (JP) ........................................ 2001-144240

(51) Int. Cl.[7] .......................... A01N 43/50; A61K 6/00; A61K 47/00; A61K 9/48; A61K 9/20

(52) U.S. Cl. ...................... 514/396; 424/400; 424/439; 424/464; 424/451; 536/1.11; 514/2; 514/23; 514/773; 514/777

(58) Field of Search ............................... 424/400, 439, 424/441, 451, 464, 520, 548; 514/396, 2, 23, 773, 777; 536/1.11

(56) References Cited

U.S. PATENT DOCUMENTS

| | | | | |
|---|---|---|---|---|
| 4,028,184 | A | * 6/1977 | Ishiyama et al. | ............... 435/92 |
| 5,391,550 | A | * 2/1995 | Carniglia et al. | ............... 514/23 |
| 5,397,786 | A | * 3/1995 | Simone | ............... 514/300 |
| 5,965,596 | A | * 10/1999 | Harris et al. | ............... 514/400 |
| 6,159,942 | A | * 12/2000 | St. Cyr et al. | ............... 514/23 |
| 6,420,342 | B1 | * 7/2002 | Hageman et al. | ............... 514/23 |

FOREIGN PATENT DOCUMENTS

| | | |
|---|---|---|
| EP | 324227 A1 | 7/1989 |
| EP | 0449787 | * 2/1991 |
| EP | 0652012 | * 11/1993 |
| EP | 0652012 | * 5/1995 |
| EP | 0 710 485 A1 | 5/1996 |

(List continued on next page.)

OTHER PUBLICATIONS

Bralley J.A. and Lord R.S., "Treatment of Chronic Fatigue Syndrome with Specific Amino Acid Supplementation", *Journal of Applied Nutrition*, vol. 46, No. 3, (1994), pp. 74–78.

R.C. Harris et al, "Elevation of creatine in resting and exercised muscle of normal subjects by creatine supplementation", *Clinical Science*, 83, pp. 367–374, (1992).

M. Suyama et al, "Chromatographic Determination of Imidazole Compounds in the Whale Meat", *Bulletin of the Japanese Society of Scientific Fisheries*, vol. 33, No. 2, pp. 141–146, (1967).

*Primary Examiner*—Gary Kunz
*Assistant Examiner*—Sharmila S Gollamudi
(74) *Attorney, Agent, or Firm*—Frishauf, Holtz, Goodman & Chick, P.C.

(57) ABSTRACT

An antifatigue composition for reducing muscular fatigue or the like during or after exercise, which includes an imidazole compound obtained from extracts of fishes, shelifishes, fowl, flesh or the like, as an active ingredient. The imidazole compound in the antifatigue composition is preferably at least one compound selected from the group consisting of histidine, anserine, carnosine, valenine and salts thereof. The antifatigue composition preferably further contains D-ribose as an active ingredient. By orally ingesting the antifatigue composition, the amount of lactic acid in plasma during or after exercise can be kept low, and therefore muscle fatigue caused by exercise can be controlled, and as a result, the ability to exercise can be improved.

20 Claims, 7 Drawing Sheets

* showed significant difference (p<0.05) as compared with all other groups

FOREIGN PATENT DOCUMENTS

| | | |
|---|---:|---|
| EP | 873754 A1 | 10/1998 |
| EP | 0 894 439 A1 | 2/1999 |
| EP | 983726 A1 | 3/2000 |
| JP | 58-165774 A | 9/1983 |
| JP | 59-210871 | 11/1984 |
| JP | 60-094075 | 5/1985 |
| JP | 61181357 * | 8/1986 |
| JP | 07-025838 A | 1/1995 |
| JP | 08-198748 A | 8/1996 |
| JP | 09020660 * | 1/1997 |
| JP | 9-020661 A | 1/1997 |
| JP | 09-249556 A | 9/1997 |
| JP | 2000-026290 A | 1/2000 |
| WO | WO 90/06102 A1 | 6/1990 |
| WO | WO 98/06278 A1 | 2/1998 |
| WO | WO 99/65476 A2 | 12/1999 |
| WO | WO 01/85178 A1 | 11/2001 |

* cited by examiner

* showed significant difference (p<0.05) as compared with the control group
** showed significant difference (p<0.01) as compared with the control group Swimming time [sec]

| No. | group 1 | group 2 | group 3 | group 4 | group 5 | group 6 | group 7 | group 8 |
|---|---|---|---|---|---|---|---|---|
| 1 | 238 | 242 | 85 | 145 | 201 | 228 | 225 | 279 |
| 2 | 162 | 102 | 151 | 109 | 303 | 262 | 181 | 181 |
| 3 | 142 | 219 | 89 | 92 | 243 | 312 | 163 | 371 |
| 4 | 95 | 148 | 214 | 358 | 164 | 372 | 199 | 426 |
| 5 | 195 | 171 | 121 | 77 | 119 | 207 | 205 | 298 |
| 6 | 125 | 113 | 101 | 214 | 189 | 103 | 174 | 375 |
| 7 | 82 | 295 | 295 | 162 | 226 | 195 | 321 | 219 |
| 8 | 218 | 194 | 192 | 258 | 392 | 136 | 221 | 342 |
| 9 | 102 | 203 | 179 | 104 | 107 | 219 | 132 | 399 |
| 10 | 205 | 98 | 249 | 295 | 265 | 289 | 285 | 356 |
| Mean | 156.4 | 178.5 | 167.6 | 181.4 | 220.9 | 232.3 | 210.6 | 324.6 |
| S.E | 17.6 | 20.5 | 22.5 | 30.3 | 27.2 | 25.4 | 17.9 | 25.0 |
| t-value(to 1) | 0 | 1.079878 | 0.497473 | 0.823985 | 2.373154 | 2.985114 | 3.02649 | 6.721527 |
| t-value(to 2) | | 0 | 0.484148 | 0.095582 | 1.560027 | 2.11593 | 1.792442 | 5.888977 |
| t-value(to 3) | | | 0 | 0.45484 | 1.961072 | 2.544623 | 2.40109 | 6.273958 |
| t-value(to 4) | | | | 0 | 1.453327 | 2.001875 | 1.630508 | 5.172483 |
| t-value(to 5) | | | | | 0 | 0.448357 | 0.575145 | 4.144009 |
| t-value(to 6) | | | | | | 0 | 1.211713 | 3.683448 |
| t-value(to 7) | | | | | | | 0 | 4.553613 |
| t-value(to 8) | | | | | | | | 0 |

The raw data for Fig.1 : The period of time in which a mouse (n=10) was able to swim in a water bath was measured in each group. The t-value in a distribution of data on the difference between each listed pair of groups were calculated by an ordinary Student's test. The indicated groups represent a control (group 1), glucose-administered (group 2), fructose-administered (group 3), ribose-administered (group 4), anserine-administered (group 5), anserine/glucose-administered (group 6), anserine/fructose-administered (group 7) and anserine/ribose-administered (group 8). Estimated from the variance of a system, t-values more than 3.499 and 2.365 indicated in shaded boxes were considered to be equivalent to p<0.01 and p<0.05, respectively. The t-values on the difference between groups of interest and depicted in Fig.1 are indicated in bold boxes.

Lactic acid conc.[mg/dl Plasma]

| No. | group 1 | group 2 | group 3 | group 4 | group 5 | group 6 | group 7 | group 8 |
|---|---|---|---|---|---|---|---|---|
| 1 | 10.6 | 28.9 | 37.2 | 12.1 | 11.4 | 15.7 | 9.1 | 13.4 |
| 2 | 33.6 | 39.5 | 11.6 | 40.5 | 30.1 | 9.1 | 32.2 | 30.9 |
| 3 | 42.6 | 47.9 | 28.4 | 26.3 | 38.4 | 36.4 | 34.2 | 32.1 |
| 4 | 11.8 | 12.6 | 46.9 | 9.8 | 13.6 | 26.2 | 16.2 | 8.2 |
| 5 | 48.9 | 22.5 | 34.6 | 34.9 | 26.1 | 28.2 | 23.1 | 21.8 |
| 6 | 43.6 | 37.3 | 24.3 | 16.8 | 36.2 | 33.5 | 27.1 | 27.8 |
| 7 | 17.9 | 43.6 | 21.6 | 10.3 | 9.8 | 13.2 | 8.2 | 7.9 |
| 8 | 27.4 | 18.6 | 13.5 | 18.1 | 10.2 | 10.1 | 18.2 | 8.6 |
| 9 | 47.9 | 29.8 | 43.5 | 31.8 | 16.3 | 19.8 | 13.4 | 26.2 |
| 10 | 20.6 | 34.5 | 48.2 | 22.4 | 15.2 | 11.3 | 28.1 | 11.2 |
| Mean | 30.5 | 31.5 | 31.0 | 22.3 | 20.7 | 20.4 | 21.0 | 18.8 |
| S.E | 4.7 | 3.6 | 4.2 | 3.4 | 3.5 | 3.2 | 3.0 | 3.1 |
| t-value(to 1) | 0 | 0.289879 | 0.116987 | 2.39957 | 2.808872 | 3.183735 | 3.218451 | 3.713838 |
| t-value(to 2) | | 0 | 0.128925 | 2.701347 | 3.105301 | 3.507132 | 3.507032 | 4.041343 |
| t-value(to 3) | | | 0 | 2.543134 | 2.949892 | 3.337584 | 3.38428 | 3.869641 |
| t-value(to 4) | | | | 0 | 0.451837 | 0.612257 | 0.446725 | 1.1097 |
| t-value(to 5) | | | | | 0 | 0.119312 | 0.084607 | 0.610494 |
| t-value(to 6) | | | | | | 0 | 0.21321 | 0.489667 |
| t-value(to 7) | | | | | | | 0 | 0.689985 |
| t-value(to 8) | | | | | | | | 0 |

The raw data for Fig.2 : The plasma concentration of the lactic acid after swimming exercise from a mouse (n=10) was measured in each group. The t-value in a distribution of data on the difference between each listed pair of groups were calculated by an ordinary Student's test. The indicated groups represent a control (group 1), glucose-administered (group 2), fructose-administered (group 3), ribose-administered (group 4), anserine-administered (group 5), anserine/glucose-administered (group 6), anserine/fructose-administered (group 7) and anserine/ribose-administered (group 8). Estimated from the variance of a system, t-values more than 3.499 and 2.365 indicated in shaded boxes were considered to be equivalent to $p<0.01$ and $p<0.05$, respectively. The t-values on the difference between groups of interest and depicted in Fig.2 are indicated in bold boxes.

* showed significant difference (p<0.05)
as compared with all other groups

\* showed significant difference (p<0.05)
  as compared with the control group
\*\* showed significant difference (p<0.01)
  as compared with the control group

US 6,855,727 B2

MUSCULAR FATIGUE-CONTROLLING COMPOSITION AND METHOD FOR PROVIDING MUSCULAR FATIGUE-CONTROLLING EFFECT

FIELD OF THE INVENTION

The present invention relates to an antifatigue composition utilizing an imidazole compound obtainable from fishes, shellfishes, fowl, flesh or the like.

BACKGROUND OF THE INVENTION

During hard exercise, glucose derived from glycogen in muscles is utilized, and anaerobic glycolytic reaction proceeds and ATP necessary for contraction of muscles is synthesized. Then, lactic acid as a metabolite is stored and intramuscular pH tends to decrease, whereby the efficiency of muscle contraction is reduced. This condition is called metabolic acidosis, and it is believed that this condition results in muscular fatigue. Accordingly, in order to control the muscular fatigue by continuous exercise, it is important not to cause metabolic acidosis.

In recent years, it is popular among athletes to intake creatine as a supplement. It is known that creatine is converted to creatine phosphate in the body and has a function of transferring energy as a high energy phosphate compound, and that creatine is a component essential for synthesis of ATP, and that by the intake of creatine, the creatine amount in muscles is increased and the performance of extreme sports or exercise will be improved (Harris, R. C. et al: Clin. Sci., 83, 367–374, 1992).

Further, if glycogen as an energy source becomes insufficient, body fat tends to be easily utilized and at the same time, amino acid in blood is converted to energy. Accordingly, it has also been attempted to increase the amino acid concentration in blood as high as possible, to utilize it as an energy source and improve the muscular fatigue and the decline of muscular strength. Particularly utilizable amino acid as the energy source is a branched amino acid (e.g. leucine, isoleucine and valine). For example, JP-A-58-165774, JP-A-7-25838 and JP-A-2000-26290 disclose the use of the above branched amino acid as foods.

Further, JP-A-8-198748 and JP-A-9-249556 disclose that for the purpose of improving athletic functions and providing effects for recovering from fatigue, the fluctuation of amino acid in blood is controlled by administering an amino acid composition constituted in accordance with the amino acids contained in saliva secreted by larvae of a verpine wasp (Vespar genus).

Incidentally, an extract obtainable from fishes, shellfishes, fowl, flesh or the like, contain various amino acids, and generally widely utilized as a seasoning. However, physiologically active functions thereof have hardly been researched.

SUMMARY OF THE INVENTION

Accordingly, it is an object of the present invention to provide a functional food material utilizing an extract obtainable from fishes, shellfishes, fowl, flesh or the like.

In the course of researches of physiologically active functions of the extract for a seasoning prepared from the meat of bonito or tuna, the present inventors have paid attention to an imidazole compound contained in said extract in a large amount, and made extensive studies on it, and as a result, found that said imidazole compound has an effect for improving the exercise performance, namely an antifatigue effect. Further, they have also found that by utilizing the imidazole compound with D-ribose in combination, more excellent antifatigue effect can be obtained, and accomplished the present invention on the basis of these facts.

Namely, the present invention provides an antifatigue composition which comprises an imidazole compound as an active ingredient.

According to the present invention, it is possible to provide an antifatigue composition by which muscular fatigue or the like during or after exercise can be reduced by utilizing an extract obtainable from fishes, shellfishes, fowl, flesh or the like and orally ingesting it

DESCRIPTION OF PREFERRED EMBODIMENTS

Figure 1:
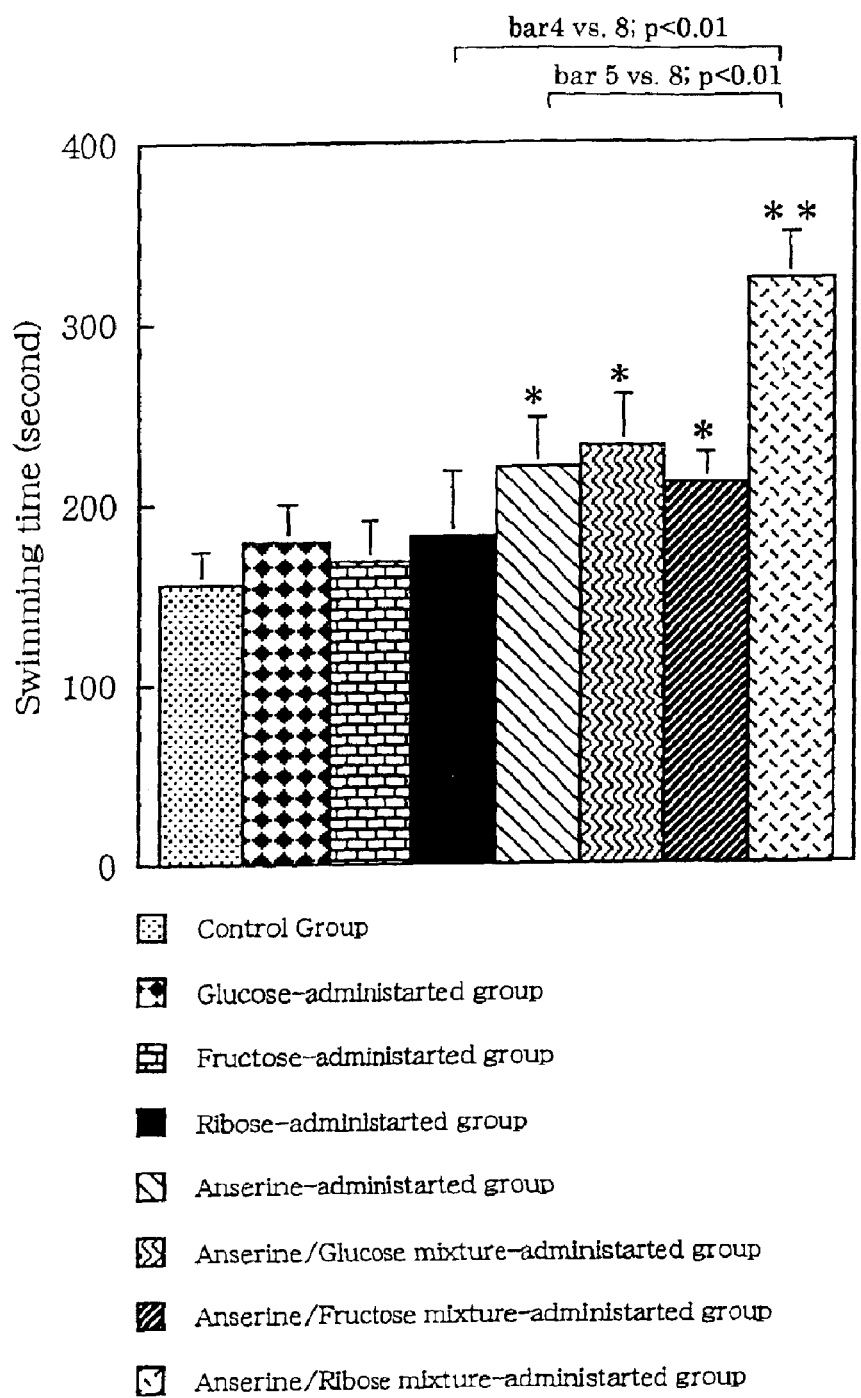
FIG. 1 is a graph showing the results of the measurement of swimming time of mice.

Hereinafter, the present invention will be described in further detail with reference to preferred embodiments.

As specific examples of the imidazole compound as the active ingredient of the antifatigue composition of the present invention, histigine, anserine (β-alanyl-1-methylhistidine), carnosine (β-alanylhistidine), valenine (β-alanyl-3-methylhistidine) and the like may be mentioned. In the present invention, it is preferred to contain as an active ingredient at least one selected from histidine, anserine, carnosine and valenine, and salts thereof. Further, as the salts, salts of hydrochloric acid, sulfuric acid, lactic acid, acetic acid, citric acid, ascorbic acid, malic acid, succinic acid, adipic acid, gluconic acid, tartaric acid and the like may be mentioned.

The above imidazole compounds are contained in fish, chicken, flesh or livestock meat, whale meat, and the like. These can be obtained by purifying an extract obtained by a method e.g. water extraction, hot water extraction, alcohol extraction or supercritical extraction.

For example, anserine is obtained in the following manner. First, an extract is prepared from the meat of bonito, tuna, cow, chicken or the like in accordance with conventional manner, the brix (Bx.) of said extract is adjusted to be 1 to 10% by adding proper amount of water, and then high molecular weight proteins are removed and low molecular weight peptide fractions are recovered by using an ultrafiltration membrane (fractionated molecular weight: 5,000 to 50,000). Then, in accordance with a manner described in a document (Suyama et al: Bull. Japan. Soc. Scient. Fish., 33, 141–146, 1967), an appropriately concentrated low molecular weight peptide fractions are subjected to an ion exchange chromatography using a strongly acidic resin, and an effluent is recovered. And, this effluent is desalted, and then the pH is adjusted, followed by freeze drying to obtain anserine.

Further, carnosine is obtainable from pork as the material and valenine is obtainable from whale meat (e.g. baleen whale) as the material, by methods similar to the above-mentioned.

The antifatigue composition of the present invention may preferably contain D-ribose as additional active ingredient. D-ribose is a monosaccharide belonging to aldopentose, and exists as nucleoside or nucleotide having phosphoric acid bonded in nature. In the present invention, commercially available ones can be used, and they may be bought from, for example, Wako Junyaku Co., Ltd.

Preferred amounts of the above active ingredients in the antifatigue composition of the present invention will be explained below.

(1) When the antifatigue composition of the present invention contains the imidazole compound alone as the active ingredient, the imidazole compound content is preferably at least 10 mass %, more preferably at least 50 mass %. If the imidazole compound content is less than 10 mass %, no adequate antifatigue effect can be expected.

(2) When the antifatigue composition of the present invention contains the imidazole compound and D-ribose as active ingredients, it is preferred to contain the imidazole compound in an amount of from 5 to 50 mass % and D-ribose in an amount of from 5 to 50 mass %. It is further preferred to contain the imidazole compound in an amount of from 10 to 50 mass % and D-ribose in an amount of from 10 to 50 mass %. If the amounts of the imidazole compound and D-ribose are outside of the above range, no synergistic antifatigue effect can be expected.

Further, the antifatigue composition of the present invention may preferably contain at least one selected from taurine, creatine, vitamin E, vitamin C, carotenoid, reduced glutathione and minerals. By containing the above components, physiologically active effects inherent to the respective components, for example, antifatigue effect of taurine, creatine and the like, and anti-oxidant effect of vitamin E, vitamin C, carotenoid and reduced glutathione and the like, can be expected. As the minerals, trace metal elements applicable to food and drink, for example, calcium, sodium, magnesium, selenium, iron, zinc and the like, may be mentioned.

The antifatigue composition of the present invention may appropriately contain an excipient, saccharides, perfume, a coloring agent, fat and oil, protein or the like, in addition to the above basic components.

The formulation as the product of the antifatigue composition of the present invention is not particularly limited, and may appropriately selected depending upon the purpose of use, for example, tablets, powder, granules, capsules, paste, solution and the like may be mentioned.

Effective intake per day of the antifatigue composition of the present invention is from 1 to 200 mg/kg of body weight, preferably from 5 to 30 mg/kg of body weight, in terms of the imidazole compound. Further, even when the imidazole compound and D-ribose are used in combination, the effective intake per day is from 1 to 200 mg/kg of body weight, preferably from 5 to 30 mg/kg of body weight, in terms of the total amount thereof.

The antifatigue composition of the present invention may be added to food and drink such as soft drinks, tablets, snack foods, powdered soup or sausage. In such a case, it is preferred to add it to the food and drink in an amount of from 100 to 2,000 mg, more preferably from 400 to 2,000 mg, in terms of the imidazole compound (or the total amount of the imidazole compound and D-ribose). If the added amount of the imidazole compound (or the total amount of the imidazole compound and D-ribose) is less than 100 mg, the antifatigue effect can not be expected so much, and if it exceeds 2,000 mg, the taste of the food and drink is affected, such being undesirable.

PREPARATION EXAMPLE 1

Preparation of Anserine

To 10 kg bonito extract (Bx.=55%) prepared in accordance with a conventional method, 4-times amount of water was added for dilution, and then by use of an ultrafiltration membrane (fractionated molecular weight: 10,000), high molecular weight proteins were removed and low molecular weight peptide fractions were recovered. The recovered fractions were concentrated and subjected to a treatment with a column chromatography filled with a strongly acidic resin (trade name "Amberlite IR-120", manufactured by Rohm & Haas Co.) equilibrated with 0.38N sodium citrate aqueous solution (pH4.0), and eluted with 0.38N sodium citrate aqueous solution (pH4.0) in an amount of from 4.5 to 6.0 times of the resin volume, and then eluted fractions were collected (reference can be made to "Suyama et al: Bull. Japan. Soc. Scient. Fish., 33, 141–146, 1967"). And, this solution was subjected to desalting and pH adjustment, and then freeze dried to obtain 45 g of powder. The obtained powder was analyzed with an amino acid analyzer manufactured by Hitachi, Ltd., whereby it was found that the purity was 98% as anserine hydrochloride.

PREPARATION EXAMPLE 2

Preparation of Carnosine

Purification was carried out in the same manner as in Example 1 except that 10 kg of an extract (Bx.=30%) prepared from pork in accordance with a conventional method, and as a result, 24 g of powder was obtained. With this powder, the purity was 92% as carnosine hydrochloride.

PREPARATION EXAMPLE 3

Preparation of Valenine

Purification was carried out in the same manner as in Example 1 except that 10 kg of an extract (Bx.=50%) prepared from baleen whale in accordance with a conventional method, and as a result, 40 g of powder was obtained. With this powder, the purity was 92% as valenine hydrochloride.

Test Example 1

20 SPF mice (male) of 6-weeks old were separated into two groups (test group and control group; each group consists of 10 mice), and after 4 hours fasting, oral administration was forcedly made so that water for injection would be applied to the control group in an amount of 200 mg/kg of body weight and an aqueous solution of the anserine hydrochloride prepared in Example 1 (40 mg/ml) would be applied to the test group in an amount of 200 mg/kg of body weight.

Accurately 1 hour after the oral administration, the mice were loaded with the following forced exercise. Mice were put into a water bath (W 265 mm×D 427 mm×H 204 mm)

containing water of 20° C., wherein the water surface was made choppy by blowing air, and the swimming time was measured. Each mouse was loaded with a weight which corresponds to 10% of the average body weight of mice, and the swimming time was represented by the time from the start of swimming until the head of the mouse submerged for at least 7 seconds.

When 3 minutes passed from the completion of the measurement of the swimming time (the first hanging time) and when 30 minutes passed from the completion of the measurement of the swimming time (the second hanging time), the mouse was let to hang from a wire and the time until it fell was measured.

Further, when 1 hour passed after the loading of exercise, the blood was collected and the plasma was separated, and the lactic acid amount in the plasma was measured. The measurement of lactic acid amount was carried out with a commercially available kit (trade name: "F-kit L-lactic acid"; manufactured by Beringer Mannheim Co.). Results of respective measurements were represented by an average value±standard deviation (n=10), and examination of significance was carried out by Studen't t-test.

FIG. 1 shows the results of the measurement of the swimming time. From FIG. 1, it is found that the test group shows a longer swimming time than the control group.

Figure 2:
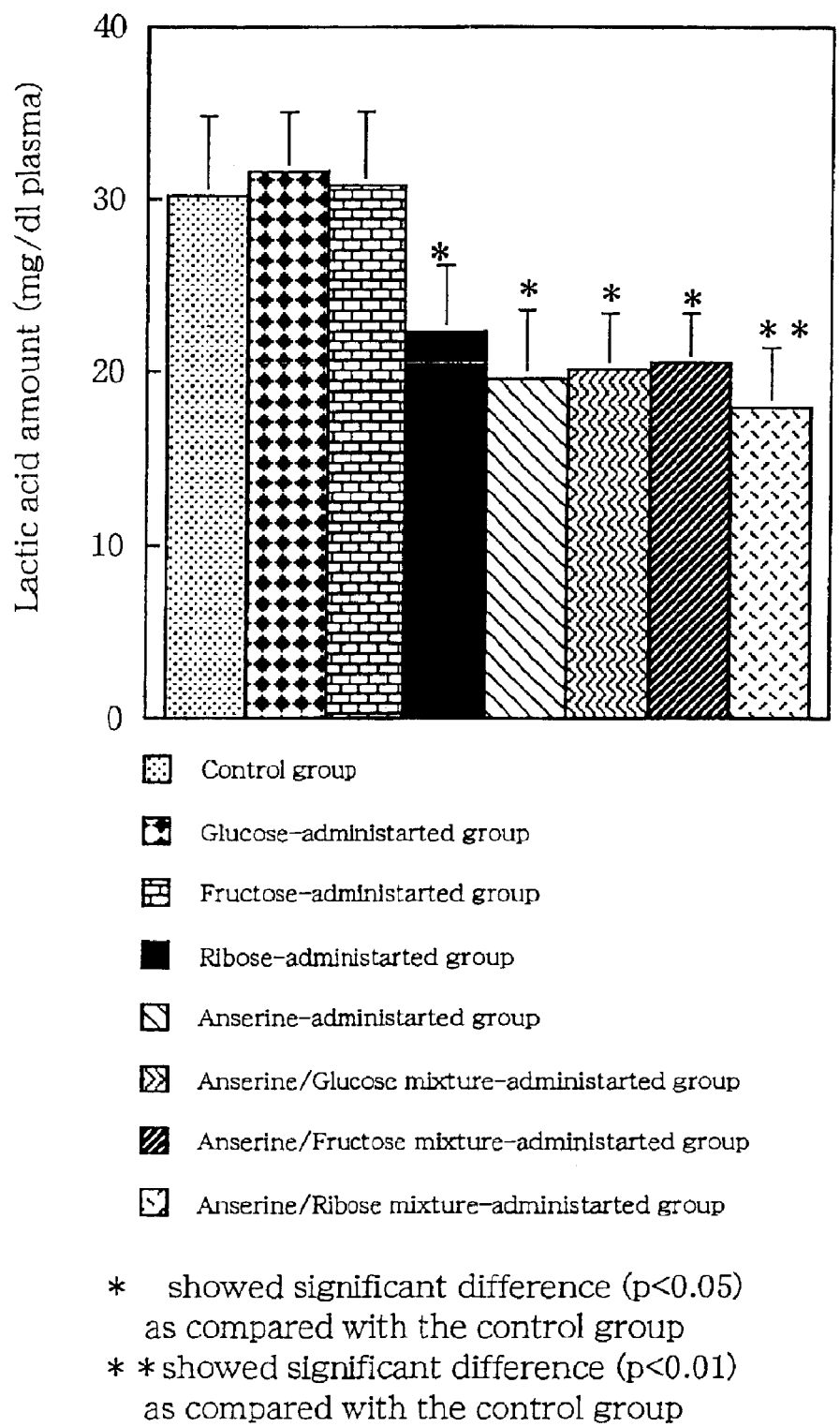
FIG. 2 is a graph showing the results of the measurement of the first hanging time of mice.
Figure 3:
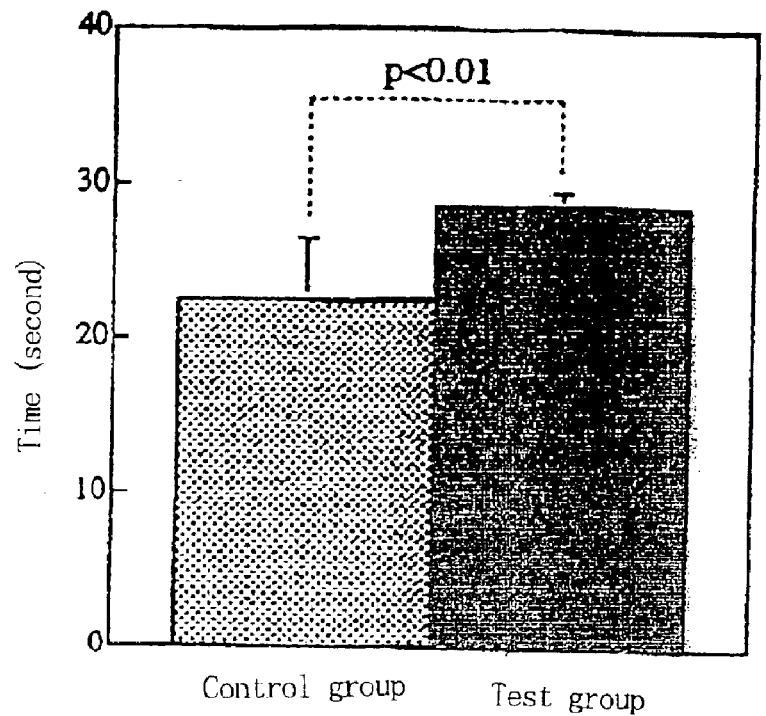
FIG. 3 is a graph showing the results of the measurement of the second hanging time of mice.

FIGS. 2 and 3 show the results of the measurements of the fist and second hanging times. From FIGS. 2 and 3, it is found that in each case, the test group shows a longer hanging-enduring time as compared with the control group. Particularly, in the second hanging time, it is found that the test group shows a longer hanging-enduring time at a level of significance ($p<0.01$) as compared with the control group.

Figure 4:
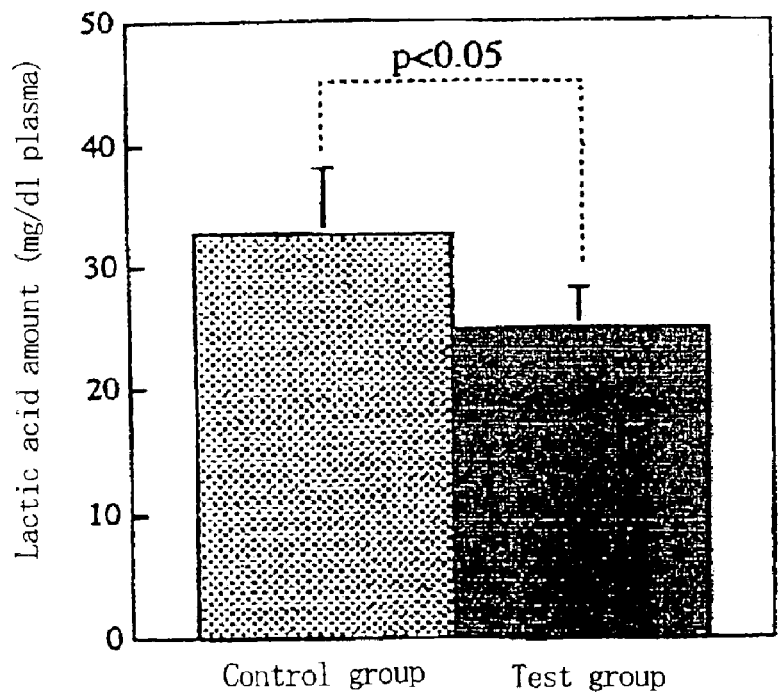
FIG. 4 is a graph showing a lactic acid amount in plasma of mice at the point that one hour passed from the loading of exercise.

FIG. 4 shows the lactic acid amount in the plasma when one hour passed from the completion of the loading of exercise. From FIG. 4, it is found that the test group shows that the lactic acid amount in the plasma thereof is kept low at a level of significance ($p<0.05$) as compared with the control group.

Test Example 2

40 SPF mice (male) of 6-weeks old were separated into four groups (control group, and test groups i.e. anserine-administrated group, ribose-administrated group and anserine/ribose mixture-administrated group; each group consists of 10 mice), and after 4 hours fasting, oral administration was forcedly made so that water for injection would be applied to the control group in an amount of 200 mg/kg of body weight; an aqueous solution of the anserine hydrochloride prepared in Example 1 (40 mg/ml) would be applied to the anserine-administrated group in an amount of 200 mg/kg of body weight in terms of anserine hydrochloride; an aqueous solution of D-ribose (40 mg/ml) would be applied to the ribose-administrated group in an amount of 200 mg/kg of body weight in terms of D-ribose; and an aqueous solution of a mixture (40 mg/ml) wherein the anserine hydrochloride and D-ribose are incorporated at a mass ratio of 1:1, would be applied to the anserine/ribose mixture-administrated group in an amount of 200 mg/kg of body weight in terms of the total amount of the anserine hydrochloride and D-ribose.

Accurately 1 hour after the oral administration, the swimming time of mice was measured in the same manner as in TEST EXAMPLE 1.

Further, when 1 hour passed after the loading of exercise, the blood was collected and the plasma was separated, and the lactic acid amount in the plasma was measured in the same manner as in TEST EXAMPLE 1. Results of respective measurements were represented by an average value±standard deviation (n=10), and examination of significant difference was carried out by Studen't t-test.

Figure 5:
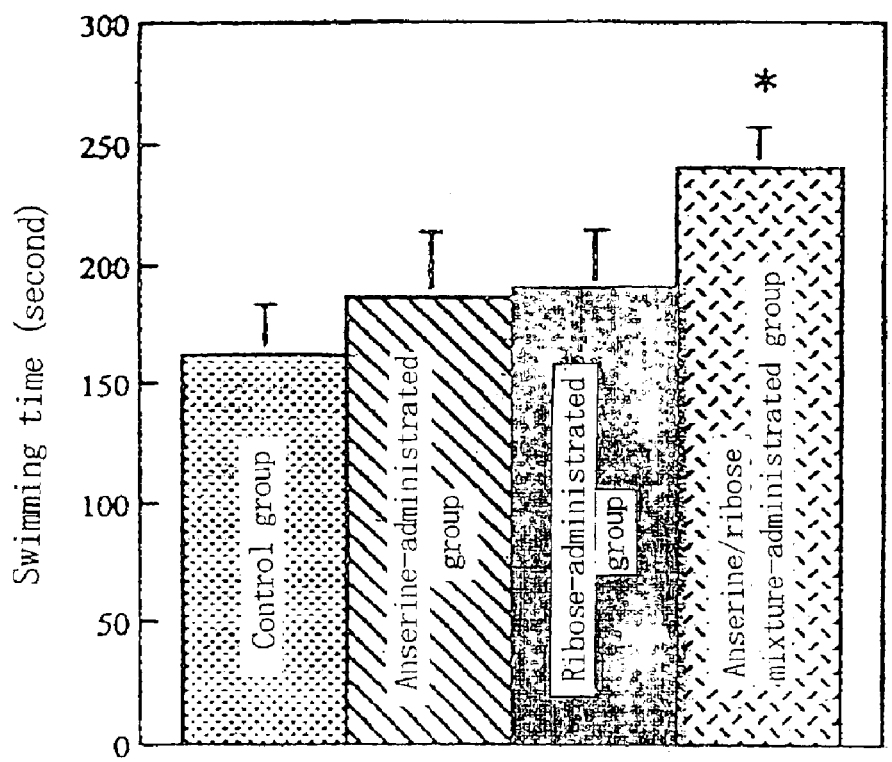
FIG. 5 is a graph showing the results of the measurement of swimming time of mice.

FIG. 5 shows the results of the swimming times of respective groups. From FIG. 5, it is found that the test groups show longer swimming times than the control group. Particularly, the anserine/ribose mixture-administrated group shows a longer swimming time at a level of significance ($p<0.05$) as compared with the other groups.

Figure 6:
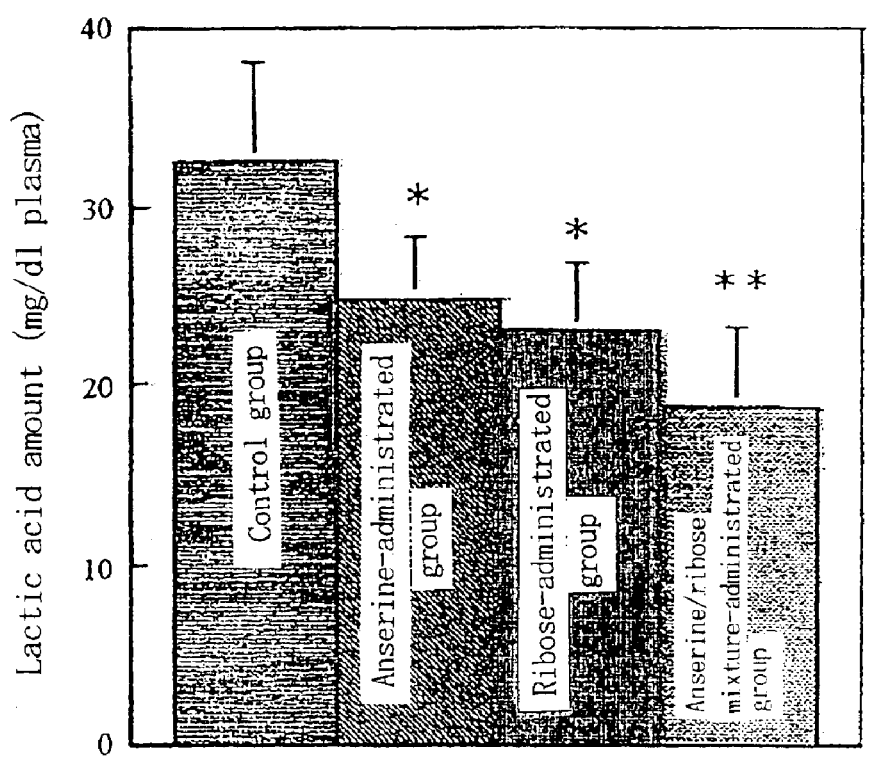
FIG. 6 is a graph showing a lactic acid amount in plasma of mice after the loading of exercise.

FIG. 6 shows the lactic acid amount in the plasma after the loading of exercise. From FIG. 6, it is found that in the anserine-administrated group (23.9% decreased) and the ribose-administrated group (29.4% decreased), the lactic acid amounts in the plasma are kept low at a level of significance ($p<0.05$) as compared with the control group. Further, it is also found that in the anserine/ribose mixture-administrated group (42.0% decreased), the lactic acid amount in the plasma is kept low at a level of significance ($p<0.01$) as compared with the control group.

From the above results, it is suggested that the exercise performance can be improved by orally ingesting anserine. Further, from the fact that the lactic acid amount in the plasma after the exercise is kept low, it is suggested that the fatigue of muscles by exercise can be suppressed or controlled. Furthermore, taking into consideration the fact that the administered amounts of respective groups (200 mg/kg of body weight) are constant, it is suggested that as compared with the cases where anserine or D-ribose is used alone, fatigue can be controlled synergistically by using anserine and D-ribose in combination.

EXAMPLES

Formulations of food and drink in which the antifatigue composition of the present invention is incorporated, are shown below. Table 1 shows the formulation of a nutrient drink for sportspersons, and Table 2 shows the formulation of a tablet.

TABLE 1

| Starting materials | Per 100 ml |
|---|---|
| Anserine (hydrochloride) | 0.5 g |
| D-ribose | 1 g |
| Taurine | 1 g |
| Vitamin C | 0.4 g |
| Liquid sugar of fructose | 10 g |
| Acidifier | Proper quantity |
| Perfume | Proper quantity |
| Preservative | Proper quantity |

TABLE 2

| Starting materials | Mass % |
|---|---|
| Anserine (hydrochloride) | 5 |
| D-ribose | 30 |
| Creatine | 2 |
| Vitamin C | 1 |
| Vitamin E | 0.1 |
| Dextrose | 20 |
| Dextrin | 33.8 |
| Minerals | 5 |
| Acidifier | 3 |
| Perfume | 0.1 |

As described above, according to the present invention, it is possible to obtain an antifatigue composition by which the lactic acid amount in plasma during or after exercise can be kept low and which is able to control the fatigue of muscles by exercise. Accordingly, by orally ingesting the antifatigue composition, muscular fatigue can be controlled and as a result, effects for improving the ability of exercise can be expected.

What is claimed is:

1. A muscular fatigue-controlling composition consisting essentially of muscular fatigue-controlling synergistic effective amounts of (a) an imidazole compound which is anserine or a salt thereof and (b) D-ribose.

2. The composition according to claim 1, wherein the imidazole compound is contained in an amount of at least 10 mass %.

3. The composition according to claim 1, wherein the imidazole compound is contained in an amount of from 5 to 50 mass % and the D-ribose is contained in an amount of from 5 to 50 mass %.

4. A muscular fatigue-controlling composition consisting essentially of (i) muscular fatigue-controlling synergistic effective amounts of (a) an imidazole compound which is anserine or a salt thereof and (b) D-ribose, and (ii) at least one substance selected from the group consisting of taurine, creatine, vitamin E, vitamin C, carotenoid, reduced glutathione and a mineral selected from the group consisting of calcium, sodium, magnesium, selenium, iron and zinc.

5. A method for providing a muscular fatigue-controlling effect comprising orally administering to a person in need thereof a muscular fatigue-controlling composition consisting essentially of synergistic effective amounts of (a) an imidazole compound which is anserine or a salt thereof and (b) D-ribose.

6. The method according to claim 5, wherein the imidazole compound is contained in an amount of at least 10 mass %.

7. The method according to claim 5, wherein the imidazole compound is contained in an amount of from 5 to 50 mass % and the D-ribose is contained in an amount of from 5 to 50 mass %.

8. A method for providing a muscular fatigue-controlling effect comprising orally administering to a person in need thereof a muscular fatigue-controlling composition consisting essentially of (i) muscular synergistic fatigue-controlling effective amounts of (a) an imidazole compound which is anserine or a salt thereof and (b) D-ribose, and (ii) at least one substance selected from the group consisting of taurine, creatine, vitamin E, vitamin C, carotenoid, reduced glutathione and a mineral selected from the group consisting of calcium, sodium, magnesium, selenium, iron and zinc.

9. The method according to claim 5, wherein the composition is administered in a dosage of 1 to 200 mg/kg of body weight per day, in terms of the imidazole compound.

10. The method according to claim 5, wherein the composition is administered in a dosage of 5 to 30 mg/kg of body weight per day, in terms of the imidazole compound.

11. The method according to claim 5, wherein the imidazole compound and the D-ribose are administered in a total daily dosage of 1 to 200 mg/kg of body weight.

12. The method according to claim 7, wherein the imidazole compound and the D-ribose are administered in a total daily dosage of 5 to 30 mg/kg of body weight.

13. The composition according to claim 1, wherein the composition further comprises an excipient.

14. The composition according to claim 1, wherein the composition further comprises a perfume.

15. The composition according to claim 1, wherein the composition further comprises a coloring agent.

16. The composition according to claim 1, wherein the composition further comprises a preservative.

17. The method according to claim 5, wherein the composition further comprises an excipient.

18. The method according to claim 5, wherein the composition further comprises a perfume.

19. The method according to claim 5, wherein the composition further comprises a coloring agent.

20. The method according to claim 5, wherein the composition further comprises a preservative.

* * * * *